United States Patent [19]
Sinnott et al.

[11] Patent Number: 6,039,955
[45] Date of Patent: Mar. 21, 2000

[54] NONTOXIC EXTRACT OF *LARREA TRIDENTATA* AND METHOD OF MAKING THE SAME

[75] Inventors: Robert A. Sinnott, Chandler; W. Dennis Clark, Phoenix, both of Ariz.; Kenneth Frank DeBoer, Belgrade, Mont.

[73] Assignee: Larreacorp, Ltd., Chandler, Ariz.

[21] Appl. No.: 09/329,359

[22] Filed: Jun. 10, 1999

Related U.S. Application Data

[62] Division of application No. 09/152,055, Sep. 11, 1998, which is a division of application No. 08/726,686, Oct. 7, 1996, Pat. No. 5,837,252

[60] Provisional application No. 60/020,946, Jul. 1, 1996.

[51] Int. Cl.$^7$ ...................................................... A61K 35/78
[52] U.S. Cl. ....................... 424/195.1; 424/451; 424/464; 424/489; 514/885; 514/886; 514/969
[58] Field of Search ................................ 424/195.1, 451, 424/464, 489; 514/885, 886, 969

[56] References Cited

U.S. PATENT DOCUMENTS

| | | | |
|---|---|---|---|
| 2,382,475 | 8/1945 | Gievold | 568/729 |
| 4,765,927 | 8/1988 | Nomura et al. | 252/400.2 |
| 4,774,229 | 9/1988 | Jordan | 514/25 |
| 4,880,637 | 11/1989 | Jordan | 424/641 |
| 5,276,060 | 1/1994 | Neiss et al. | 514/731 |
| 5,837,252 | 11/1998 | Sinnott et al. | 424/195.1 |
| 5,945,106 | 8/1999 | Sinnott | 424/195.1 |

*Primary Examiner*—Leon B. Lankford, Jr.
*Assistant Examiner*—Christopher R. Tate
*Attorney, Agent, or Firm*—David K. Benson

[57] ABSTRACT

A nontoxic, therapeutic agent having pharmacological activity comprising concentrated extract of *Larrea tridentata* plant material and ascorbic acid, an ascorbic acid ester, an ascorbic acid salt, butylated hydroxyanisole, butylated hydroxytoluene, hydrogen sulfide, hypophosphorous acid, monothioglycerol, potassium bisulfite, propyl gallate, sodium bisulfite, sodium hydrosulfite, sodium thiosulfate, sulfur dioxide, sulfurous acid, a tocopherol or vitamin E is made by a process in which the plant material is extracted using an organic solvent, preferably acetone, and is then saturated with one of the listed reducing agents acid to reduce the toxic NDGA quinone, which naturally occurs in the plant material, to NDGA itself. Additional amounts of ascorbic acid, an ascorbic acid ester, an ascorbic acid salt, butylated hydroxyanisole, butylated hydroxytoluene, hydrogen sulfide, hypophosphorous acid, monothioglycerol, potassium bisulfite, propyl gallate, sodium bisulfite, sodium hydrosulfite, sodium thiosulfate, sulfur dioxide, sulfurous acid, a tocopherol, or vitamin E may be added to the extract to inhibit the natural oxidation of the NDGA into the toxic NDGA quinone in vivo, or during processing or storage. The resulting extract is usefull in the treatment of viral diseases caused by viruses from the Herpesviridae family or viruses which require the Sp1 class of proteins to initiate viral replications. The resulting compound can also be used as an anti-inflammatory when the inflammatory diseases are mediated by the effects of leukotrienes. The listed reducing agents can also be used to stabilize NDGA as a therapeutic agent or a food additive.

10 Claims, 5 Drawing Sheets

NONTOXIC EXTRACT OF *LARREA TRIDENTATA* AND METHOD OF MAKING THE SAME

This application is a divisional of application Ser. No. 09/152,055, filed Sep. 11, 1998 which is a divisional of application Ser. No. 08/726,686 filed Oct. 7, 1996, now U.S. Pat. No. 5,837,252. This application also claims the priority benefit of provisional application Ser. No. 60/020,946, filed Jul. 1, 1996.

FIELD OF THE INVENTION

The present invention relates generally to a nontoxic exit of *Larrea tridentata* plant material having therapeutic value and a method of making the same. The present invention also relates to the field of nontoxic, stable NDGA products used as food additives and therapeutic agents.

BACKGROUND OF THE INVENTION

*Larrea tridentata* also known as *Larrea divericata*, Larrea, chaparral, or creosote bush, is a shrubby plant which dominates some areas of the desert southwest in the United States and Northern Mexico as well as some desert areas of Argentina. Tea made from the leaves of *Larrea tridentata* has long been used in folk medicine to treat digestive disorders, rheumatism, venereal disease, sores, bronchitis, chicken pox, and the common cold.

According to Masayuki Sakakibara, et al., *Flavonoid Methyl Ethers on the External Leaf Surface of Larrea Tridentata and L. Divaricata* in PHYTOCHEMISTRY, vol. 15, pp. 727–731 (Pergamon Press 1976), the disclosure of which is incorporated herein by reference, the natural products on the surface of the *Larrea tridentata* leaves, the leaf resin, constitutes approximately 10–15% of the dry weight of the leaves and is composed of approximately 50% nordihydroguaiaretic acid ("NDGA") and related lignans, and 50% flavonoids. NDGA, extracted from *Larrea tridentata* by an alkaline extraction method (U.S. Pat. No. 2,382,475, incorporated herein by reference) and produced synthetically (U.S. Pat. No. 2,644,822, incorporated herein by reference) was used as an antioxidant in edible fats, butter, oils and oleaginous materials (U.S. Pat. No. 2,373,192, incorporated herein by reference), until the GRAS (Generally Recognized As Safe) status of NDGA was revoked after animal studies revealed evidence of kidney toxicity resulting from the ingestion of NDGA.

NDGA is known as a powerful antioxidant compound. However, NDGA can itself be oxidized to toxic oxidation products by chemical means or by oxidation during processing and storage. A highly reactive and toxic oxidation product of NDGA is nordihydroguaiaretic acid ortho di-a-b-unsaturated quinone ("NDGA quinone"), which according to T. J. Mabry et al., *The Natural Products Chemistry of Larrea* in CREOSOTE BUSH: BIOLOGY AND CHEMISTRY OF LARREA IN THE NEW WORLD DESERT, ch. 5, pp. 115–133 (Dowden, Hutchinson and Ross, Pennsylvania 1977) (incorporated herein by reference), occurs in Larrea and Larrea extracts and probably serves as a toxin to protect the plant from being eaten by herbivores. According to a recent report by FDA scientists (W. R. Obermeyer et al., *Chemical Studies of Phytoestrogens and Related Compounds in Dietary Supplements: Flax and Chaparral*, 208 PROC. SOC. EXP. BIOL. MED., pp. 6–12 (1995), the disclosure of which is incorporated herein by reference), NDGA quinone is found in chaparral (*Larrea tridentata*) and is suspected to be a causative agent of the toxic effects associated with consumption of chaparral products.

NDGA is the dominant lignan present in *Larrea tridentata*. NDGA is known to possess a variety of biological effects including anti-tumor activity, enzyme inhibition activity and antimicrobial activity according to W. Donald MacRae & G. H. Neil Towers, *Biological Activities of Lignans*, PHYTOCHEMISTRY, vol. 23, pp. 1207–1220 (Pergamon Press 1984)(incorporated herein by reference). Additionally, NDGA and other antioxidants have been shown to be potent inhibitors of the human immunodeficiency virus type 1 (HIV) transcription. The mode of action of this anti-HIV activity was suggested to be due to the potent antioxidant activity of NDGA inhibiting a redox regulated signal transduction pathway leading to production of HIV virus.

More recently, three scientific articles, John N. Gnabre et al., *Inhibition of human immunodeficiency virus type 1 transcription and replication by DNA sequence-selective plant lignans*, PROC. NATL. ACAD. SCI., USA, vol. 92, pp. 11239–11243 (November 1995); John Gnabre et al., *Characterization of Anti-HIV Lignans from Larrea tridentata*, TETRAHEDRON, vol. 51, pp. 12203–12210 (1995); and John Noel Gnabre et al., *Isolation of anti-HIV-1 lignans from Larrea tridentata by counter-current chromatography*, JOURNAL OF CHROMATOGRAPHY A, vol 719, pp. 353–364 (1996), the disclosure of all three articles being incorporated herein by reference, demonstrate that at least two lignans isolated from *Larrea tridentata*, NDGA and 3-O-methyl nordihydroguaiaretic acid ("Mal. 4") inhibit transcription and replication of human immunodeficiency virus type 1 by a novel mechanism. This elucidated mechanism of anti-HIV activity is thought to be due to the ability of the two identified *Larrea tridentata* lignans, NDGA and Mal. 4, to interfere with the binding of the Sp1 protein to Sp1 binding sites in the HIV long terminal repeat (HIV-LTR). According to this theory, by inhibiting Sp1 binding in the HIV-LTR, the promoter activity of the HIV-LTR is eliminated so that HIV transcription, HIV Tat-regulated transactivation and HIV replication do not occur. It is further theorized by the authors that viruses other than HIV, which require binding of Sp1 protein in promoter-contaning Sp1 binding sites to initiate viral replication, might also be inhibited by the anti-HIV lignans isolated from *Larrea tridentata* and that this class of lignans, in general, may possess a broader antiviral action of important interest.

Also, in a recent article, Anneke K. Raney & Alan McLachlan, *Characterization of the Hepatitis B Virus Large Surface Antigen Promoter Sp1 Binding Site*, VIROLOGY, vol. 208, pp. 399–404 (1995), binding sites for the transcription factor Sp1 have been identified in the DNA promoter regions of at least two important viral genes of the Hepatitis B virus (HBV) which may be involved in the coordinate regulation of HBV transcription by transcription factor Sp1.

Kaposi's Sarcoma, a cancer that frequently occurs among AIDS patients, has recently been implicated to be caused by a new herpes virus, human herpes virus-8 (HHV-8). See Roland G. Nador et al., *Primary Effusion Lymphoma: A Distinct Clinicopathologic Entity Associated With the Kaposi's Sarcoma—Associated Herpes Virus*, BLOOD, vol. 88, no. 2, pp. 645–656 (Jul. 15, 1996), incorporated herein by reference. See also, Matt Crenson, *Kaposi's Sarcoma is tied to herpes*, THE PHILADELPHIA INQUIRER, p. A4 (Jul. 31, 1996), and Lawrence K. Altman, *Aids Cancer Said to Have Viral Source: Breakthrough Seen in Kaposi's Sarcoma*, NEW YORK TIMES §A, p. 22 (Feb. 1, 1995), incorporated herein by reference.

Certain flavonoid compounds, especially members of the chemical classes flavones and flavonols can inhibit HIV activation at fairly low concentrations (See , J. William Critchfield et al., *Inhibition of HIV Activation in Latently infected Cells by Flavonoid Compounds"* in AIDS *Research and Human Retroviruses*, AIDS RESEARCH AND HUMAN RETROVIRUSES, vol. 12, no. 1, pp. 39–46 (1996), incorporated herein by reference). As further cited in Masayuki Sakakibara, et al., *Flavonoid Methyl Ethers on the External Leaf Surface of Larrea Tridentata and L. Divaricata* in PHYTOCHEMISTRY, vol. 15, pp. 727–731 (Pergamon Press 1976), *Larrea tridentata* contains an abundance of these classes of antiviral flavonoids, particularly methyl ethers of flavonols.

Like many physiologically active chemicals isolated from plant sources, these antiviral lignans and flavonoid compounds appear to work synergistically with other unresolved compounds present in crude extracts of *Larrea tridentata*. The identity and mode of action of these synergistic compounds is unknown but they may facilitate absorption of the antiviral lignans or otherwise enhance the specific physiological antiviral effects.

NDGA is known to be a potent inhibitor of the enzyme 5-lipoxygenase. One of the enzymatic products of 5-lipoxygenase is 5-hydroperoxyeicosatetraenoic acid (HPETE) which is the precursor compound for the biosynthesis of very potent chemical mediators of inflammation, known as leukotrienes. As detailed in William R. Henderson, *The Role of Leukotrienes in Inflammation*, ANN. INTER. MED., vol. 121, pp. 684–697 (1994), the disclosure of which is incorporated herein by reference, 5-lipoxygenase is limited to a specific number of myeloid cells including: neutrophils, eosinophils, monocytes, macrophages, mast cells, basophils and B-lymphocytes. Leukotrienes are chemicals which induce prolonged muscle contraction, especially in the bronchioles of the lungs, and also increase vascular permeability and attract neutrophils and eosinophils to the site of inflammation. The leukotrienes play a major role in the inflammatory response to injury. Leukotrienes have also been implicated in the pathogenesis of several inflammatory diseases including: asthma, psoriasis, rheumatoid arthritis and inflammatory bowel disease. The role of leukotrienes as mediators of inflammatory diseases makes them attractive targets for therapeutic drugs to treat these diseases.

Many inhibitors of leukotriene synthesis are being developed. Recently, a 5-lipoxygenase inhibitor, Zileuton, was found to be effective in the treatment of asthma during clinical tests (Elliot Israel et al., *Effect of Treatment With Zileuton, a 5-lipoxygenase Inhibitor, in Patients with Asthma*, JAMA, vol 275, pp. 931–936 (Mar. 27, 1996), the disclosure of which is incorporated herein by reference). The success of Zileuton underscores the utility and need of therapeutic agents containing 5-lipoxygenase inhibitors in the treatment of inflammatory disease processes, including asthma.

Throughout this specification and claims, viral diseases are intended to include all diseases, attributed to a pathological virus of humans or animals, in which the causative viral agent which requires the Sp1 class of proteins to initiate viral replication, including certain viral agents of venereal diseases such as the Herpes viruses (the Herpesviridae), HSV-1 and HSV-2, viral hepatitis (the Hepadnaviridae) such as hepatitis B, and members of the retrovirus family (the retroviridae) including Varicella-Zoster viruses, cytomegalovirus (CMV), the human T-lymphotrophic viruses 1 and 2 (HTLV-1 and (HTLV-2) the human immunodeficiency viruses 1 and 2 (HIV-1 and HIV-2) and the cancer Kaposi's Sarcoma. Inflammatory diseases, throughout the specification and claims, are intended to include all diseases in which leukotrienes are known to play a major role or have been implicated including: asthma, allergic rhinitis, psoriasis, rheumatoid arthritis, inflammatory bowel disease, inflammatory pain, cystic fibrosis, adult respiratory distress syndrome, glomerulonephritis, inflammation of the skin, and virally induced inflammation (caused by CMV and other members of the Herpesviridae) leading to atherosclerosis/arteriosclerosis and subsequent coronary artery disease.

In light of the foregoing background, there exists the need for a commercial method of producing a *Larrea tridentata* extract which contains a high concentration of both the identified antiviral lignans (NDGA and Mal. 4), flavonoids, and a wide variety of other associated organic compounds from the leaf resin, which may contribute synergistic antiviral and lipoxygenase inhibitory activity.

Additionally, for the purpose of toxicological safety, it is of critical importance that the *Larrea tridentata* extract to be used for medical applications, be processed to reduce the concentration of the toxic compound, NDGA quinone, which is reported to occur naturally in *Larrea tridentata* plant tissues. There is also a need to inhibit the natural production of toxic oxidation products, such as NDGA quinone, in the *Larrea tridentata* extract during processing and storage of the extract and formulated products and to facilitate the processing of the concentrated extract as either a liquid, slurry, or solid.

Lastly, there is a need for products comprising synthesized NDGA which is stabilized against oxidation into NDGA quinone during processing and storage.

SUMMARY OF THE INVENTION

Accordingly, it is an object of the present invention to meet the above described needs and others. It is an object of the present invention to provide a nontoxic extract of *Larrea tridentata* having a high concentration of NDGA. It is a further object of the present invention to provide a nontoxic extract of *Larrea tridentata* containing Mal. 4 and other compounds having known or expected, and perhaps synergistic, therapeutic effects.

It is a further object of the present invention to provide such an extract which contains little or no NDGA quinone and which inhibits the production of NDGA quinone in vivo and during processing and storage. It is a further object of the present invention to provide a method of making the above-described extract, and formulations thereof. It is a further object of the present invention to describe some of the potential therapeutic uses of the above-described extract, and formulations thereof.

It is a further object of the present invention to provide NDGA products for use as food additives or therapeutic agents in which the NDGA is prevented during storage and processing from oxidizing into NDGA quinone.

Additional objects, advantages and novel features of the invention will be set forth in the description which follows or may be learned by those skilled in the art through reading these materials or practicing the invention. The objects and advantages of the invention may be achieved through the means recited in the attached claims.

To achieve the stated and other objects of the present invention, as embodied and described below, the invention may comprise:

A method of preparing a nontoxic extract of *Larrea tridentata* plant material comprising the steps of:
extracting endogenous antiviral and anti-inflammatory lignans and flavonoids and other synergistic compounds from *Larrea tridentata* plant material with a polar solvent, preferably acetone, to produce an extract by recirculating the solvent over the plant material a plurality of times;

filtering the extract;

adding an emulsifying and stabilizing agent, preferably polysorbate 80, to the filtered extract;

reducing the NDGA quinone in the extract with ascorbic acid, ascorbic acid esters (i.e. ascorbyl palmitate), ascorbic acid salts (i.e. sodium ascorbate), butylated hydroxyanisole (BHA), butylated hydroxytoluene (BHT), hydrogen sulfide, hypophosphorous acid (phosphinic acid), monothioglycerol (3 mercapto-1,2-propanediol), potassium bisulfite (potassium metabisulfite, potassium pyrosulfite), propyl gallate, sodium bisulfite (sodium metabisulfite, sodium pyrosulfite), sodium hydrosulfite (sodium dithionite), sodium thiosulfate (sodium hyposulfite), sulfur dioxide, suilfrous acid, a tocopherol, or vitamin E (DL-alpha-tocopherol), preferably ascorbic acid, by passing the extract through a bed of ascorbic acid powder;

boiling the organic solvent out of the compound; and adding additional amounts of one of the above listed reducing agents to the compound subsequent to the step of reducing.

The present invention may also comprise:

A nontoxic, therapeutic agent comprising:

an extract of *Larrea tridentata* plant material comprising NDGA and Mal. 4; and ascorbic acid, ascorbic acid esters (i.e. ascorbyl palmitate), ascorbic acid salts (i.e. sodium ascorbate), butylated hydroxyanisole (BHA), butylated hydroxytoluene (BHT), hydrogen sulfide, hypophosphorous acid (phosphinic acid), monothioglycerol (3 mercapto-1,2-propanediol), potassium bisulfite (potassium metabisulfite, potassium pyrosulfite), propyl gallate, sodium bisulfite (sodium metabisulfite, sodium pyrosulfite), sodium hydrosulfite (sodium dithionite), sodium thiosulfate (sodium hyposulfite), sulfur dioxide, suilfrous acid, a tocopherol, or vitamin E (DL-alpha-tocopherol).

The present invention may also comprise:

formulations of the described therapeutic agent in the embodiment of a lotion, liquid, powder or pill.

The present invention may also comprise a food additive or therapeutic agent comprising:

NDGA; and ascorbic acid, ascorbic acid esters (i.e. ascorbyl palmitate), ascorbic acid salts (i.e. sodium ascorbate), butylated hydroxyanisole (BHA), butylated hydroxytoluene (BHT), hydrogen sulfide, hypophosphorous acid (phosphinic acid), monothioglycerol (3 mercapto-1,2-propanediol), potassium bisuifite (potassium metabisulfite, potassium pyrosulfite), propyl gallate, sodium bisulfite (sodium metabisulfite, sodium pyrosulfite), sodium hydrosulfite (sodium dithionite), sodium thiosulfate (sodium hyposulfite), sulfur dioxide, sulfurous acid, a tocopherol, or vitamin E (DL-alpha-tocopherol).

The present invention may also comprise:

A method of treating:

Viral diseases caused by viruses from the retrovirus family of viruses, the Hepatitis B virus, the Herpesviridae family of viruses, and viruses which require Sp1 class proteins to initiate viral replication, inflammatory diseases which are mediated by the effects of leukotrienes, and virally induced imflammation leading to atherosclerosis, hypertension, atherosclerosis, arteriosclerosis, and subsequent coronary artery disease using a nontoxic, therapeutic agent comprising:

an extract of *Larrea tridentata* plant material comprising NDGA and Mal. 4; and ascorbic acid, ascorbic acid esters (i.e. asorbyl palmitate), ascorbic acid salts (i.e. sodium ascorbate), butylated hydroxyanisole (BHA), butylatd hydroxytoluene (BHT), hydrogen sulfide, hypophosphorous acid (phosphinic acid), monothioglyceol (3 mercapto-1,2-propanediol), potassium bisulfite (potassium metabisulfite, potassium pyrosulfite), propyl gallate, sodium bisulfite (sodium metabisulfite, sodium pyrosulfite), sodium hydrosulfite (sodium dithionite), sodium bisulfite (sodium hyposulfite), sulfur dioxide, sulfurous acid, a tocopherol, or vitamin E (DL-alpha-tocopherol).

BRIEF DESCRIPTION OF THE DRAWINGS

The accompanying drawings illustrate the present invention and are a part of the specification. Together will the following description, the drawings demonstrate and explain the principles of the present invention. In the drawings.

DETAILED DESCRIPTION OF THE PREFERRED EMBODIMENT

Figure 1:
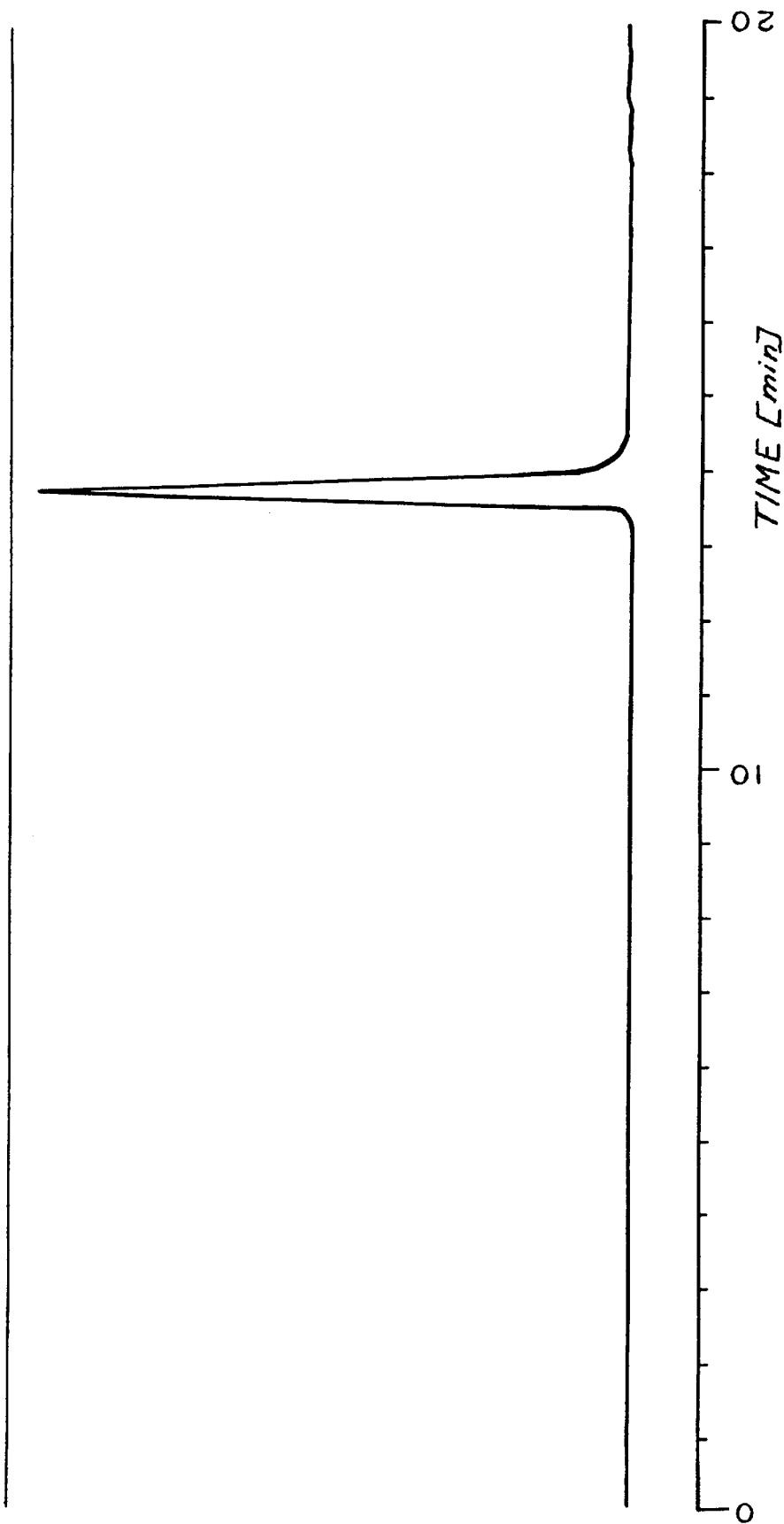
FIG. 1 is a high performance liquid chromatography ("HPLC") tracing of NDGA, as a purified compound (reported by the manufacturer to have a minimum purity of 90%). Slight amounts of unidentified impurities, probably methylated NDGA compounds, are indicated. However, no NDGA quinone is detectable in the sample. The tracing was taken at 280 nm absorbance.
Figure 2:
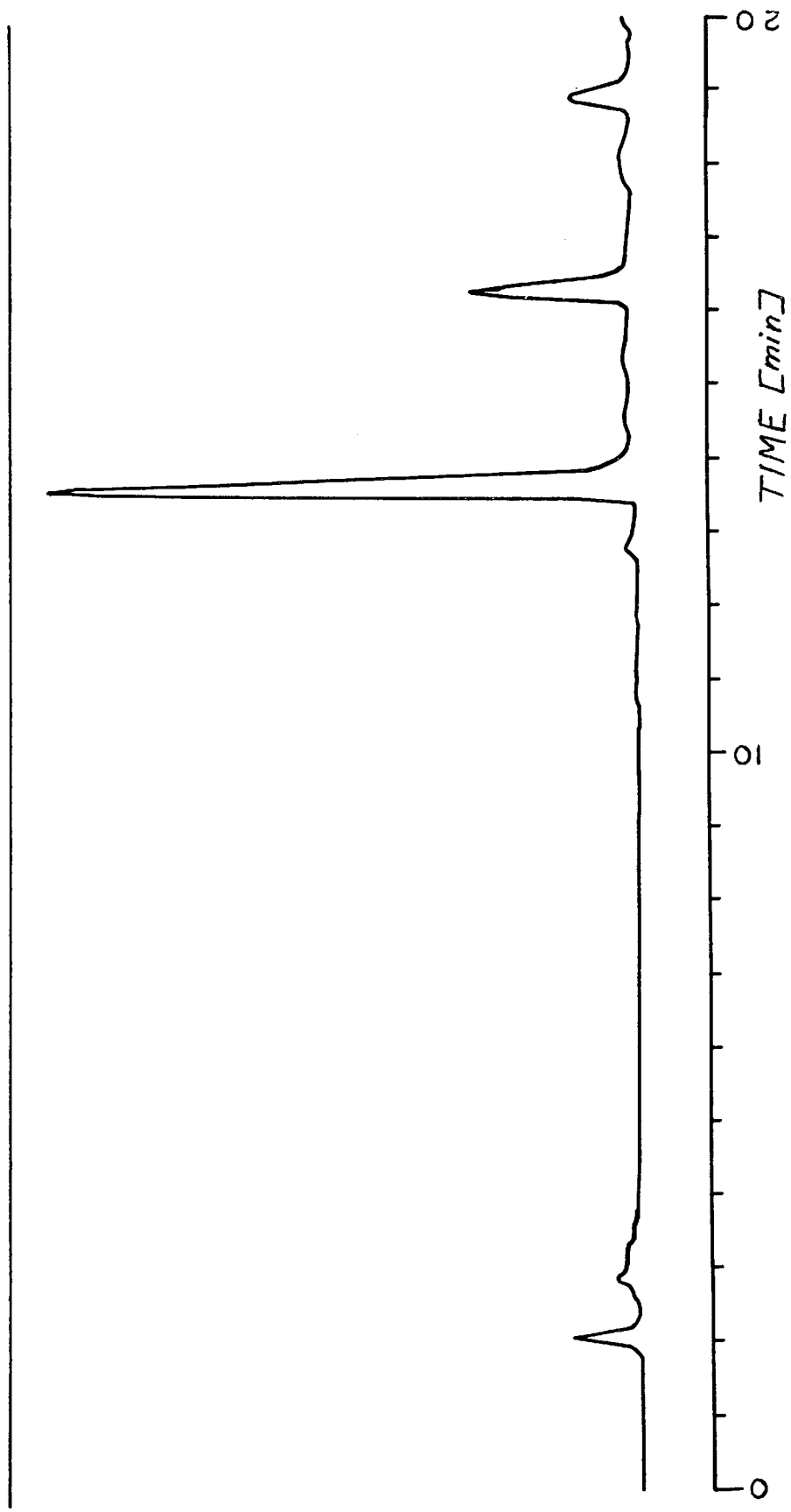
FIG. 2 is a HPLC tracing of NDGA as a purified compounds described in reference to FIG. 1 which has been treated with the strong oxidizing agents sulfuric acid and potassium dichromate. NDGA quinone, the oxidation product of NDGA, is identified in the chromatogram as the large peak at 16.5 minutes. The tracing was taken at 280 nm absorbance.
Figure 3:
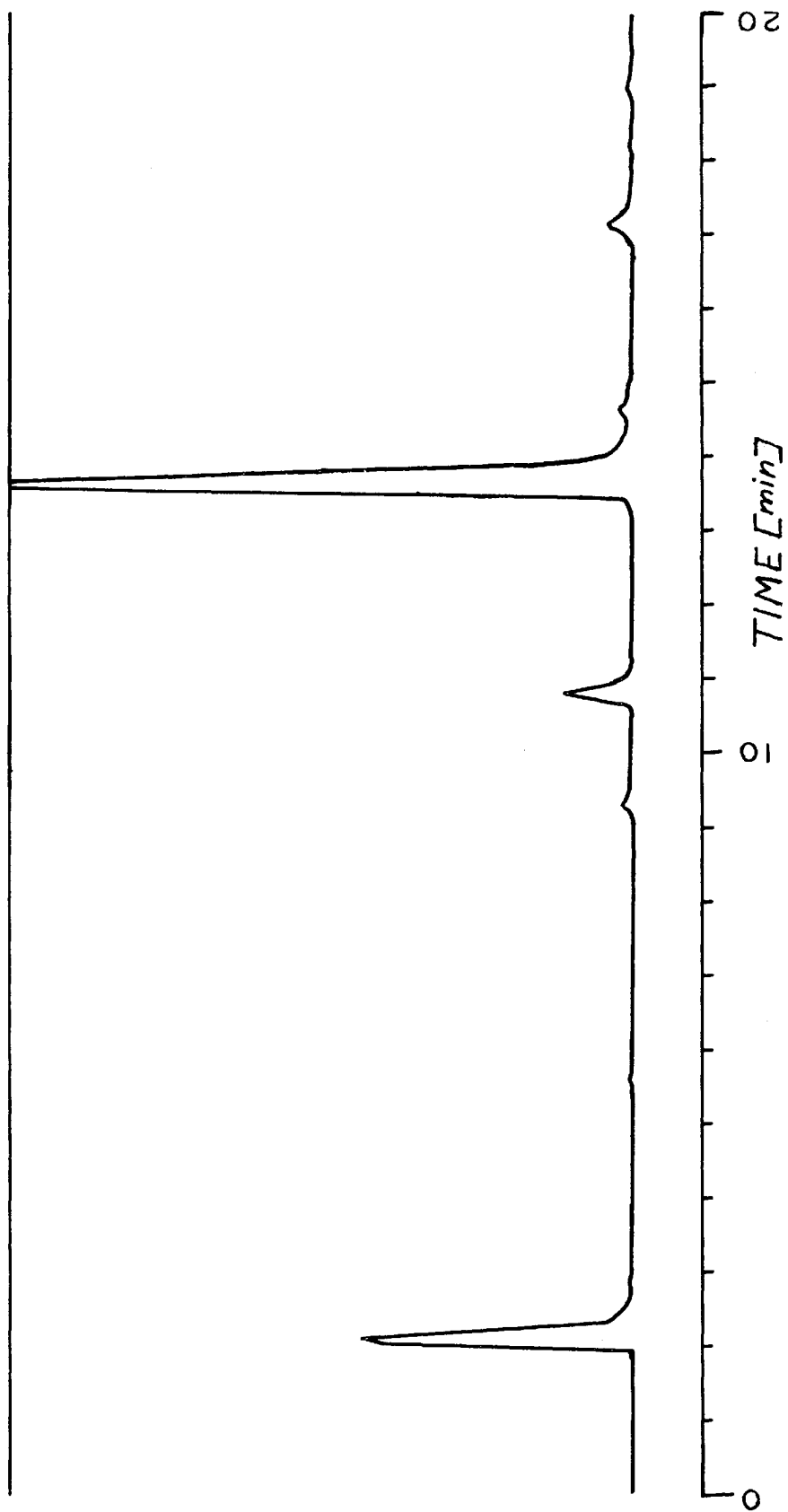
FIG. 3 is an HPLC tracing of a purified NDGA sample as described in reference to FIG. 1 and treated with oxidizing agents as described in reference to FIG. 2, and then treated according to the principles of the present invention, with the chemical reducing agent, ascorbic acid. NDGA quinone is not detectable at 16.5 minutes after treatment was completed. The tracing was taken at 280 nm absorbance.
Figure 4:
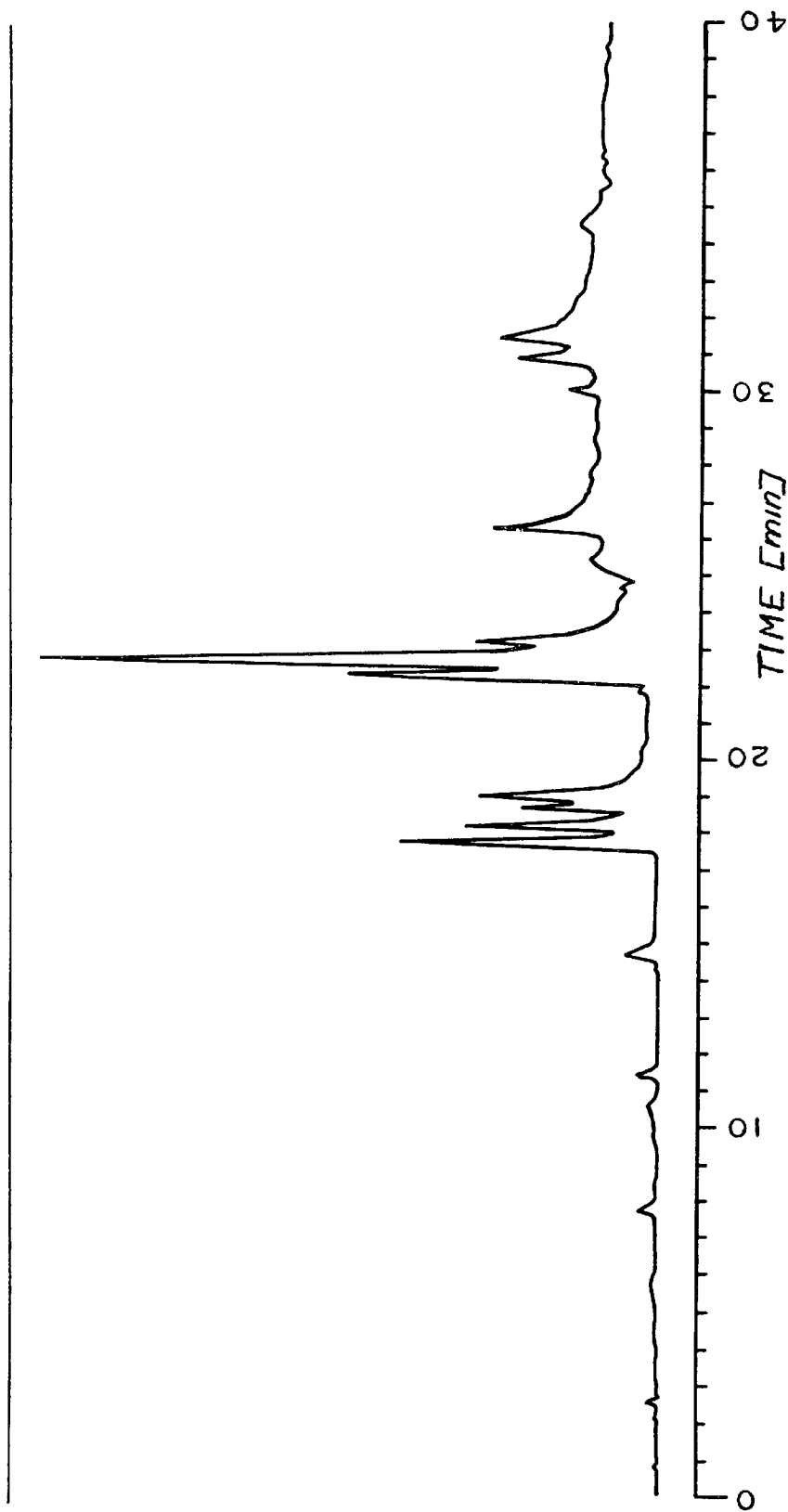
FIG. 4 is an HPLC tracing of a concentrated *Larrea tridentata* extract, which has been treated with the strong oxidizing agents sulfuric acids and potassium dichromatic. A peak corresponding with NDGA quinone is identified in the chromatogram as the small peak occurring at 30 minutes. The tracing was taken at 375 nm absorbance.
Figure 5:
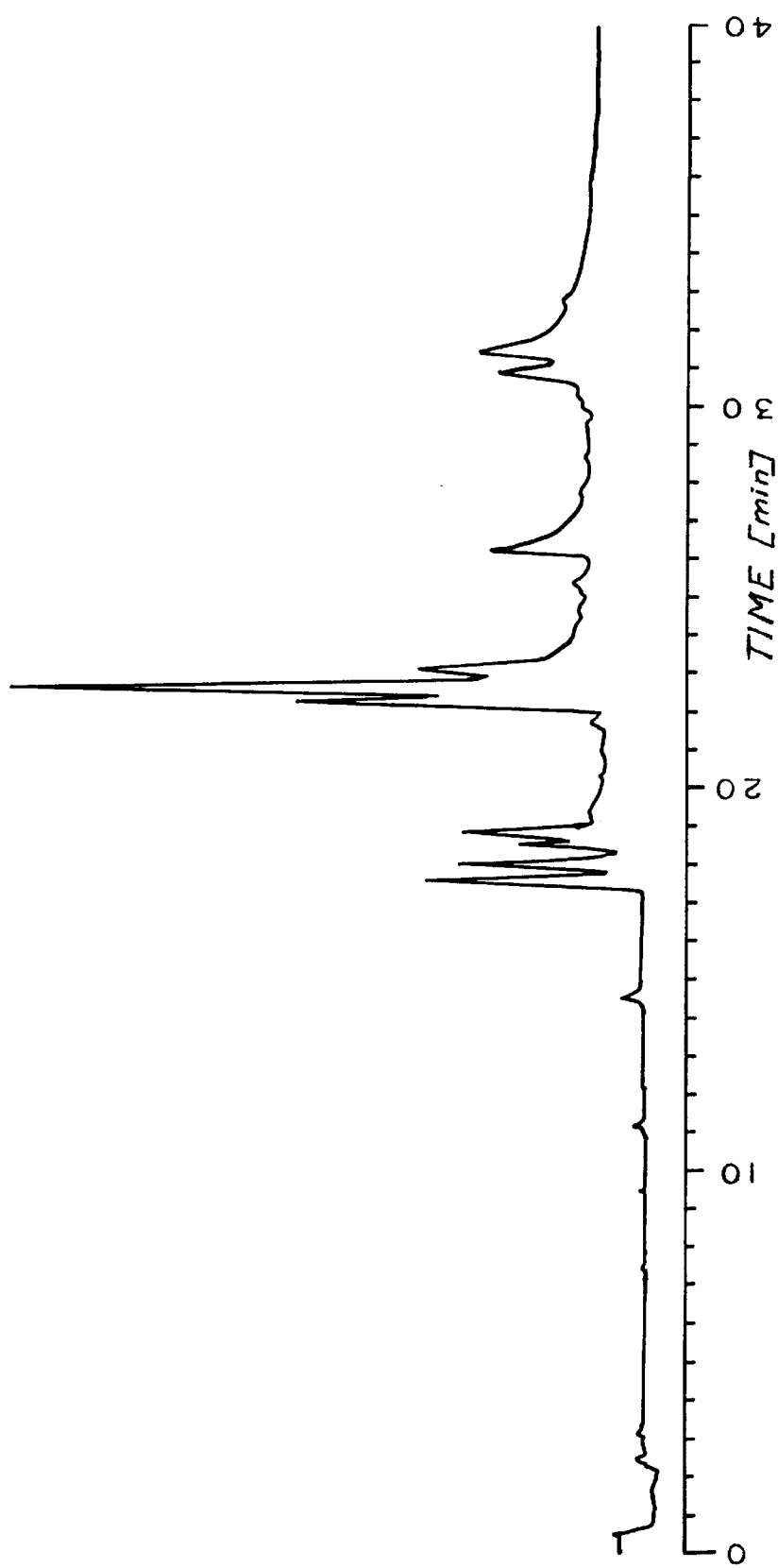
FIG. 5 is an HPLC tracing of a concentrated *Larrea tridentata* extract, produced according to the methods of the preset invention. No NDGA quinone peak is observed at 30 minutes. The tracing was taken at 375 nm absorbance.

The present invention includes at least two products.

(1) a nontoxic extract of *Larrea tridentata* plant material having a high concentration of NDGA and little or no NDGA quinone which can be used as a therapeutic agent; and (2) NDGA, for use as a food additive or therapeutic agent, which does not oxidize into NDGA quinone during storage or processing.

An important principle of the invention is that ascorbic acid, ascorbic acid esters (i.e. ascorbyl palmitate), ascorbic acid salts (ie. sodium ascorbate), butylated hydroxyanisole (BHA), butylatd hydroxytoluene (BHT), hydrogen sulfide, hypophosphorous acid (phosphinic acid), monothioglycerol (3 mercapto-1,2-propanediol), potassium bisulfite (potassium metabisulfite, potassium pyrosulfite), propyl gallate, sodium bisulfite (sodium metabisulfite, sodium pyrosulfite), sodium hydrosulfite (sodium dithionite), sodium thiosulfate (sodium hyposulfite), sulfur dioxide, sulfurous acid, a tocopherol, or vitamin E (DL-alpha-tocopherol), when combined with NDGA, reduce any NDGA quinone present into NDGA, and prevent the NDGA from oxidizing and producing more NDGA quinone. These agents are not necessarily considered to be equivalents to each other, some having advantages not possessed by all the others. It is only asserted that each of these listed agents may be used according to the principles of the invention as described in this specification to substantially accomplish the objects of the invention. The preferred embodiment of the invention will be described below.

According to the principles of the present invention, a nontoxic extract of *Larrea tridentata* having a high concentration of NDGA and very little or no NDGA quinone can be prepared by saturating the extract with one or more of the above listed agents. Additional amounts of one of the listed agents may be added to the extract or products formulated therefrom to inhibit the natural oxidation of component NDGA into NDGA quinone during processing and storage.

According to the preferred embodiment of the present invention, a nontoxic extract is prepared by the following method. *Larrea tridentata* plant material consisting mostly of leaves and stems, but also possibly containing a small amount of flowers and fruits, i.e. whole plant material, is air dried. The dried plant material is extracted using a suitable solvent. In the preferred embodiment, the solvent is an organic solvent, preferably acetone.

The organic solvent is recirculated three times over the correct ratio of plant material to completely dissolve the organic compounds on the surface of the plant material and to produce a crude *Larrea tridentata* extract. The resulting crude extract is filtered through cellulosic media (i.e. qualitative grade filter paper) to remove dirt and particulates. A chemical emulsifying and stabilizing agent, Food Chemicals Codex (F.C.C.) grade polysorbate 80, is added to the clarified extract at a concentration of 0.01% by volume.

The clarified extract is then passed through a bed of ascorbic acid powder (5 grams of F.C.C. grade ascorbic acid powder for each liter of extract passed through) in a manner which facilitates contact of the extract with the ascorbic acid powder and results in saturation of the extract with ascorbic acid. Saturating the extract with the chemical reducing agent, ascorbic acid results in conditions which favor the chemical reduction of the toxic, oxidative metabolites of NDGA, which are present in *Larrea tridentata* plant tissues and the resulting extracts. By chemically reacting with the ascorbic acid, the toxic NDGA quinones are reduced to NDGA hydroquinone which is NDGA itself.

To concentrate the *Larrea tridentata* organic extract which is saturated with ascorbic acid, the extract is transferred to a water jacketed, stainless steel tank, which is heated to approximately 100 degrees C. by circulation of a suitable solvent (i.e. water). While the extract is heated in the tank, the organic solvent is boiled out of the extract and may be recovered by condensation for reuse. The extract is heated in the tank to approximately 10 degrees above the boiling point of the organic extraction solvent. This rise in temperature of the extract indicates that the concentrated *Larrea tridentata* extract is substantially free of the extraction solvent. The concentrated extract, approximately 1/10 the volume of the original *Larrea tridentata* extract, is then removed from the tank and packaged in tightly sealed plastic drums for storage and shipping.

Another aspect of the present invention includes mixing the concentrated *Larrea tridentata* extract with effective, additional amounts of ascorbic acid, ascorbic acid esters (i.e. ascorbyl palmitate), ascorbic acid salts (i.e. sodium ascorbate), butylated hydroxyanisole (BHA), butylated hydroxytoluene (BHT), hydrogen sulfide, hypophosphorous acid (phosphinic acid), monothioglycerol (3 mercapto-1,2-propanediol), potassium bisulfite (potassium metabisulfite, potassium pyrosulfite), propyl gallate, sodium bisulfite (sodium metabisulfite, sodium pyrosulfite), sodium hydrosulfite (sodium dithionite), sodium thiosulfate (sodium hyposulfite), sulfur dioxide, sulfurous acid, a tocopherol or vitamin E (DL-alpha-tocopherol). Formulation of the extract with excess amounts of one or more of the listed reducing agents prevents subsequent formation of NDGA quinone during subsequent processing, storage, and formulating of the extract, and functions as a synergistic antioxidant in vivo with NDGA and other endogenous antiviral compounds.

Our invention is based in part on our discovery that a *Larrea tridentata* extract, which is produced according to the methods of our invention, contains no detectable amount of NDGA quinone when analyzed by high performance liquid chromatography. Because of the foregoing discussion linking NDGA quinone with the toxic effects associated with the consumption of *Larrea tridentata* products, the production of *Larrea tridentata* extract, with a very low concentration of NDGA quinone, for use in medical formulations is very important.

Further, we have found through experiments performed by the inventors, that formulations based on the *Larrea tridentata* extract and ascorbic acid compound, as described in this invention, have pronounced antiviral activity against Herpes simplex virus types 1 and 2, and against Kaposi's Sarcoma in human patients. We have also found through experimentation that the described formulations have pronounced antiviral activity against Herpes simplex virus type 1 (HSV-1) in both animal cell culture models and human volunteers as well as anti-inflammatory action in human volunteers.

The present invention therefore provides methods for the medically useful and effective extract of *Larrea tridentata* and formulations for production of pharmaceutical agents which have immediate and commercially important utility in the medical treatment of viral and inflammatory diseases.

Experimental Results:

The following are provided by way of illustrating examples of extraction and processing formulations of the *Larrea tridentata* extract, and are provided by way of illustration only and are not intended to limit the invention in any way.

EXAMPLE 1

Plant material (consisting of mostly leaves but with some small branches and a small amount of fruits and flowers) was harvested from *Larrea tridentata* shrubs growing in the Arizona desert southwest of Gila Bend, Ariz. The plant material was air dried in the shade at ambient temperature and humidity for one week before processing. 100 kg of plant material was extracted with 100 liters of F.C.C. grade acetone by recirculating the acetone over the plant material three times. The resulting *Larrea tridentata* extract was filtered through Whatan #1 filter paper.

5 mils of F.C.C. grade polysorbate 80 was added to 50 liters of the extract and the extract was slowly passed through a glass column packed with 250 g of powdered ascorbic acid. The extract, saturated with ascorbic acid, was concentrated by boiling off the acetone solvent in a water-jacketed stainless steel tank, which was heated to approximately 100 degrees Celsius by circulating hot water. The resulting concentrated extract, in the form of a viscous liquid, was collected in plastic drums and used to prepare medical formulations.

EXAMPLE 2

Several formulations of concentrated Larrea extract suitable for encapsulation were prepared by thoroughly mixing the concentrated extract, as produced in example 1, with dry excipient materials including starch, sucrose, fructose, and ascorbic acid powder. In some cases, other ingredients including antiviral and anti-inflammatory agents or herbal extracts i.e. Echinacea, Podophyllin, etc. were also combined in formulations. In all cases, the mixtures consisted of one part concentrated *Larrea tridentata* extract with 5 to 10 parts dry excipient material. These formulations were used to treat HIV opportunistic infections, and Herpes virus infections described in this specification. The treatment consisted of administering several capsules containing 50 to 100 mg of *Larrea tridentata* extract per capsule which were ingested daily.

EXAMPLE 3

Several formulations of concentrated *Larrea tridentata* extract in a lotion base were prepared by adding the concentrated extract, as produced in example 1, into various lotion formulations. The concentration of extract added to the lotion base can range from 0.1 to 5% volume/volume. In initial trial with human volunteers, a 3% lotion prepared according to the principles of the present invention has been used successfully in the medical treatment of athletes foot, viral lesions caused by herpes simplex virus (HSV-1, HSV-2), Kaposi's Sarcoma, and inflammation of the skin induced by contact allergens, ultraviolet light and thermal exposure. The treatment consisted of applying the lotion frequently and liberally to the affected areas.

EXAMPLE 4

Results obtained by the inventors show that the concentrated Larrea extract, produced by the methods of the present invention, when used at a concentration greater than 20 micrograms per milliliter, is nearly 100% effective in protecting African Green Monkey kidney cells from destruction by the Herpes simplex-1 virus (HSV-1).

It is apparent from the evidence presented above that the methods and compositions of the present invention meet long-standing needs in the medical treatment of viral and inflammatory diseases.

Many alternatives to the most preferred embodiment, described above, are also part of the present invention. For example, when the NDGA quinone is reduced using ascorbic acid, ascorbic acid esters (i.e. ascorbyl palmitate), ascorbic acid salts (i.e. sodium ascorbate), butylated hydroxyanisole (BHA), butylated hydroxytoluene (BHT), hydrogen sulfide, hypophosphorous acid (phosphinic acid), monothioglycerol (3 mercapto-1,2-propanediol), potassium bisulfite (potassium metabisulfite, potassium pyrosulfite), propyl gallate, sodium bisulfite (sodium metabisulfite, sodium pyrosulfite), sodium hydrosulfite (sodium dithionite), sodium thiosulfate (sodium hyposulfite), sulfur dioxide, sulfurous acid, a tocopherol, or vitamin E (DL-alpha-tocopherol) in a *Larrea tridentata* extract, it is not essential to add further amounts of one of these listed reducing agents as described. While doing so provides a more stable nontoxic product, if additional amounts of one or more of these listed reducing agents are not added, the resulting extract will still have use as a nontoxic therapeutic agent.

Moreover, it is not essential to use any of the listed reducing agents to reduce the NDGA quinone present initially in the extract. If another, perhaps even toxic, reducing agent is used to reduce the NDGA quinone naturally occurring in the *Larrea tridentata* extract, ascorbic acid, ascorbic acid esters (i.e. ascorbyl palmitate), ascorbic acid salts (ie. sodium ascorbate), butylated hydroxyanisole (BHA), butylated hydroxytoluene (BHT), hydrogen sulfide, hypophosphorous acid (phosphinic acid), monothioglycerol (3 mercapto-1,2-propanediol), potassium bisulfite (potassium metabisulfite, potassium pyrosulfite), propyl gallate, sodium bisulfite (sodium metabisulfite, sodium pyrosulfite), sodium hydrosulfite (sodium dithionite), sodium thiosulfate (sodium hyposulfite), sulfur dioxide, sulfurous acid, a tocopherol, or vitamin E (DL-alpha-tocopherol) can then be added to the resulting product to produce a nontoxic extract which will not develop quantities of NDGA quinone through oxidation during processing and storage. In such a process, an additional step to remove the reducing agent would likely be necessary.

Finally, as noted in the prior art NDGA has many known uses as an antioxidant food additive and as a therapeutic agent. NDGA for these purposes can be produced by extraction from natural sources, such as the *Larrea tridentata*, or can be synthesized. However the NDGA is produced, during processing and storage it oxidizes to produce NDGA quinone and is therefore toxic when ingested. Accordingly, it is within the scope of the invention to combine NDGA, whether extracted or synthesized, with ascorbic acid, ascorbic acid esters (i.e. ascorbyl palmitate), ascorbic acid salts (i.e. sodium ascorbate), butylated hydroxyanisole (BHA), butylated hydroxytoluene (BHT), hydrogen sulfide, hypophosphorous acid (phosphinic acid), monothioglycerol (3 mercapto-1,2-propanediol), potassium bisulfite (potassium metabisulfite, potassium pyrosulfite), propyl gallate, sodium bisulfite (sodium metabisulfite, sodium pyrosulfite), sodium hydrosulfite (sodium dithionite), sodium thiosulfate (sodium hyposulfite), sulfur dioxide, sulfurous acid, a tocopherol, or vitamin E (DL-alpha-tocopherol) to produce a stable, nontoxic NDGA product that can be used as a food additive or therapeutic agent.

The preceding description has been presented only to illustrate and describe the invention. It is not intended to be exhaustive or to limit the invention to any precise form disclosed. Many modifications and variations are possible in light of the above teaching.

The preferred embodiment was chosen and described in order to best explain the principles of the invention and its practical application. The preceding description is intended to enable others skilled in the art to best utilize the invention in various embodiments and with various modifications as are suited to the particular use contemplated. It is intended that the scope of the invention be defined by the following claims.

What is claimed is:

1. An agent for treatment of inflammation, comprising a concentrated extract of reduced NDGA-containing *Larrea tridentata* plant material and ascorbic acid, wherein the NDGA is reduced as a result of a chemical reaction between said extract and said ascorbic acid such that said ascorbic acid is provided at a concentration sufficient to saturate said extract prior to the concentration of said extract.

2. The agent of claim 1, further comprising an extract of Echinacea or Podophyllin.

3. The agent of claim 1, wherein said concentrated extract further comprises a dry excipient to make a pill, a capsule or a powder.

4. The agent of claim 1, further comprising a compound selected from the group consisting of a corticosteroid, an anesthetic, a nonsteroidal antiinflammatory, an antiinflammatory fatty acid and a substance P antagonist.

5. The agent of claim 1, in the form of a lotion, or a liquid.

6. The agent of claim 1, wherein said inflammation is caused by an inflammatory disease which is mediated by an effect of leukotrienes.

7. The agent of claim 6, wherein said disease is asthma, psoriases, allergic rhinitis, rheumatiod arthritis, inflammatory bowel disease, inflammatory pain, cystic fibrosis, adult respiratory distress syndrome, glomerulonephritis, inflammation of the skin, or virally induced inflammation.

8. The agent of claim 1, wherein said inflammation is induced by any of contact allergens, ultraviolet light, and thermal exposure.

9. A method of treating inflammation comprising administering to a human in need thereof, an effective amount of the agent of claim 1.

10. The method of claim 9, wherein said administering comprises topically applying said agent to an affected area of said human.

* * * * *